(12) United States Patent
Drinkard

(10) Patent No.: US 10,456,816 B1
(45) Date of Patent: Oct. 29, 2019

(54) DEMILITARIZATION OF HC SMOKE ORDNANCES

(71) Applicant: William F. Drinkard, Charlotte, NC (US)

(72) Inventor: William F. Drinkard, Charlotte, NC (US)

( * ) Notice: Subject to any disclaimer, the term of this patent is extended or adjusted under 35 U.S.C. 154(b) by 0 days.

(21) Appl. No.: 15/861,837

(22) Filed: Jan. 4, 2018

Related U.S. Application Data

(60) Provisional application No. 62/500,572, filed on May 3, 2017.

(51) Int. Cl.
| | | |
|---|---|---|
| *B09B 3/00* | (2006.01) | |
| *C07C 17/38* | (2006.01) | |
| *F42B 33/06* | (2006.01) | |
| *B01D 11/02* | (2006.01) | |
| *C01G 9/02* | (2006.01) | |

(52) U.S. Cl.
CPC ........ *B09B 3/0016* (2013.01); *B01D 11/0215* (2013.01); *B01D 11/0288* (2013.01); *C01G 9/02* (2013.01); *C07C 17/38* (2013.01); *F42B 33/06* (2013.01)

(58) Field of Classification Search
CPC ..... B09B 3/00; B09B 3/0016; B01D 11/0215; B01D 11/0288; C01G 9/02; C07C 17/38
USPC .......................................................... 588/300
See application file for complete search history.

(56) References Cited

U.S. PATENT DOCUMENTS

| | | | | |
|---|---|---|---|---|
| 4,580,447 A | * | 4/1986 | Boutros | .................. F42B 35/00 73/167 |
| 9,879,962 B2 | * | 1/2018 | Ueda | ....................... F42B 33/06 |

* cited by examiner

*Primary Examiner* — Edward M Johnson
(74) *Attorney, Agent, or Firm* — Ralph H. Dougherty

(57) ABSTRACT

An improved method for the demilitarization of HC smoke ordnance comprising hexachloroethane (HCE), zinc oxide, and granular aluminum in a metal container, the method comprising opening the container and extracting the HCE by contact with a suitable solvent which solubilizes and extracts the HCE from the remaining zinc oxide and aluminum, rendering the materials safe for further handling or disposal.

15 Claims, 2 Drawing Sheets

DEMILITARIZATION OF HC SMOKE ORDNANCES

CROSS REFERENCE TO RELATED APPLICATION

This application claims the benefit of priority of U.S. Provisional Patent Application Ser. No. 62/500,572, filed May 3, 2017.

FIELD OF THE INVENTION

The present invention relates to a method and apparatus for demilitarization of HC smoke ordnances.

BACKGROUND OF THE INVENTION

The US Military refers to certain devices as "producing HC smoke", e.g., grenades, smoke pots, and artillery shells are used to produce HC smoke. Soldiers and munition plant workers can be exposed to HC smoke and its volatile components. HC Smoke is produced by the combustion of a mixture of three primary reagents: hexachloroethane, zinc oxide, and granular aluminum. The hexachloroethane (HCE) and ZnO are mixed proportionally at about a 1:1 ratio comprising of between 90-94% of the total composition for the reactive mixture. The remainder of the composition is granular aluminum (Al) metal (6-10%). When the smoke pots or other HC smoke munitions are set off, toxic vapors that include Zinc Oxide, Zinc Chloride, Hydrochloric acid, Phosgene (carbon oxychloride—$COCl_2$), and other chlorinated vapors are released into the air. Other metals, such as lead, cadmium, arsenic, and mercury, have also been reported in HC smoke.

Prior research on the disposal of HC smoke pots was focused on thermal techniques. The smoke bombs were heated in a carbon steel rotary kiln, reacting the HCE with the zinc oxide producing environmentally hazardous emissions as described above. The aluminum metal ended up as aluminum oxide. A large number of wet scrubbers with caustic soda had to be used to neutralize the produced acid vapors, and to absorb any gases. All this requires a high price tag in disposal fees.

SUMMARY OF THE INVENTION

Military weapons, whether ordnance or chemical such as HC smoke generating weapons are designed for reliability. Operational failure may result in loss of life or failure to complete a mission. With the emphasis on reliable (fail safe) operation, inactivation and disposal of such ordnances are often difficult and expensive.

The invented methods have demonstrated to not only deliver safe disassembly of HC smoke generating reactants, but also to allow their recovery as materials that may enter commerce, reducing costs of disposal and eliminating toxic co-products such as phosgene and toxic metal content such as lead, arsenic, mercury, and cadmium in the generated HC smoke.

The invention provides a method for the demilitarization of HC smoke ordnances comprising hexachloroethane (HCE), zinc oxide, and granular aluminum in a metal container, The container is opened or penetrated and the HCE is contacted by a suitable solvent such as chloroform which solubilizes and extracts the HCE from the remaining zinc oxide and aluminum. The solvent must have a boiling point significantly below that required to ignite HC smoke mix. The solvent should have a boiling point at least 30° C. less than the temperature below that required to ignite HC smoke mix, and preferably at least 60° C. less than the temperature below that required to ignite HC smoke mix. The solvent is vaporized and removed, leaving a extracted HCE in solid form, which is recovered. A method that works well is to open or penetrate the container with a hole near its center, injecting solvent as a flushing agent through the hole into the interior of the container. A small hole may be made in or near the bottom of the container to allow the solvent or flushing agent to flow out therethrough.

OBJECTS OF THE INVENTION

The principal object of the present invention is to provide a method for deactivating HC smoke ordnances and rendering them harmless to the environment.

Another object of the invention is to provide a method for recovery of HCE, zinc values and aluminum metal from HC smoke ordnances.

BRIEF DESCRIPTION OF THE DRAWINGS

The foregoing and other objects will become more readily apparent by referring to the following detailed description and the appended drawings in which.

DETAILED DESCRIPTION

Figure 1:
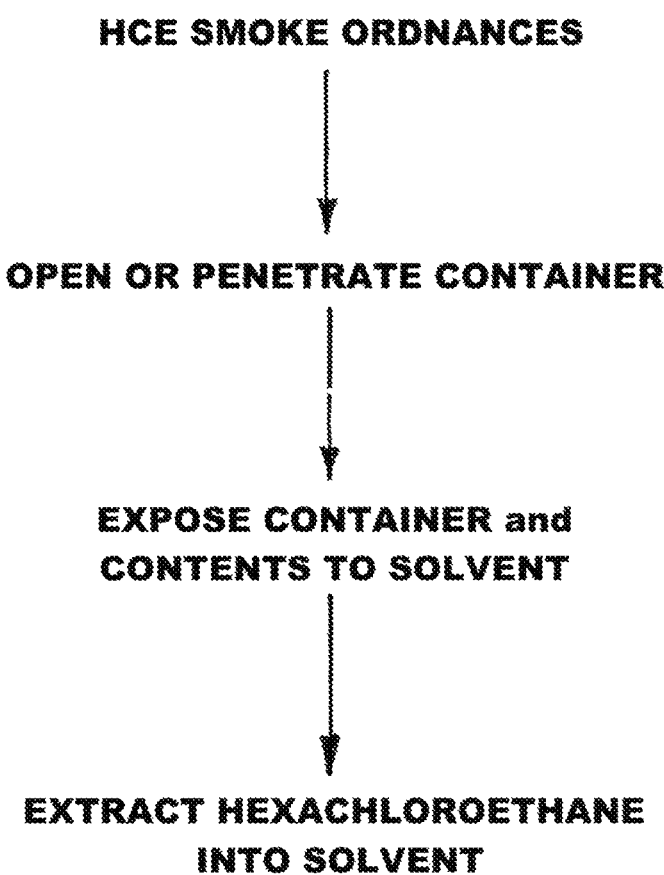
FIG. 1 is a schematic drawing of the basic steps of the invented method.

In order to accomplish the demilitarization of HC smoke ordnances comprising a reactive mixture of hexachloroethane (HCE), zinc oxide, and granular aluminum, it is necessary to separate one of the reactants from the reactive mixture. This can be either the HCE or the zinc oxide. The remaining constituents are not self-sustainingly reactive, with the exception of environmentally hazardous elements sometimes added with impure zinc oxide. The HCE is the only regulated substance and therefore upon its removal, as shown in FIG. 1, the balance of the constituents may be disposed of in a landfill, provided the fuse and igniter are first deactivated. The fuse and igniter, which are normally less than one percent of the ordnance, can be deactivated by effective hydration, and can be verified to be nonreactive by heating to above the activation temperature of 300° C.

Figure 2:
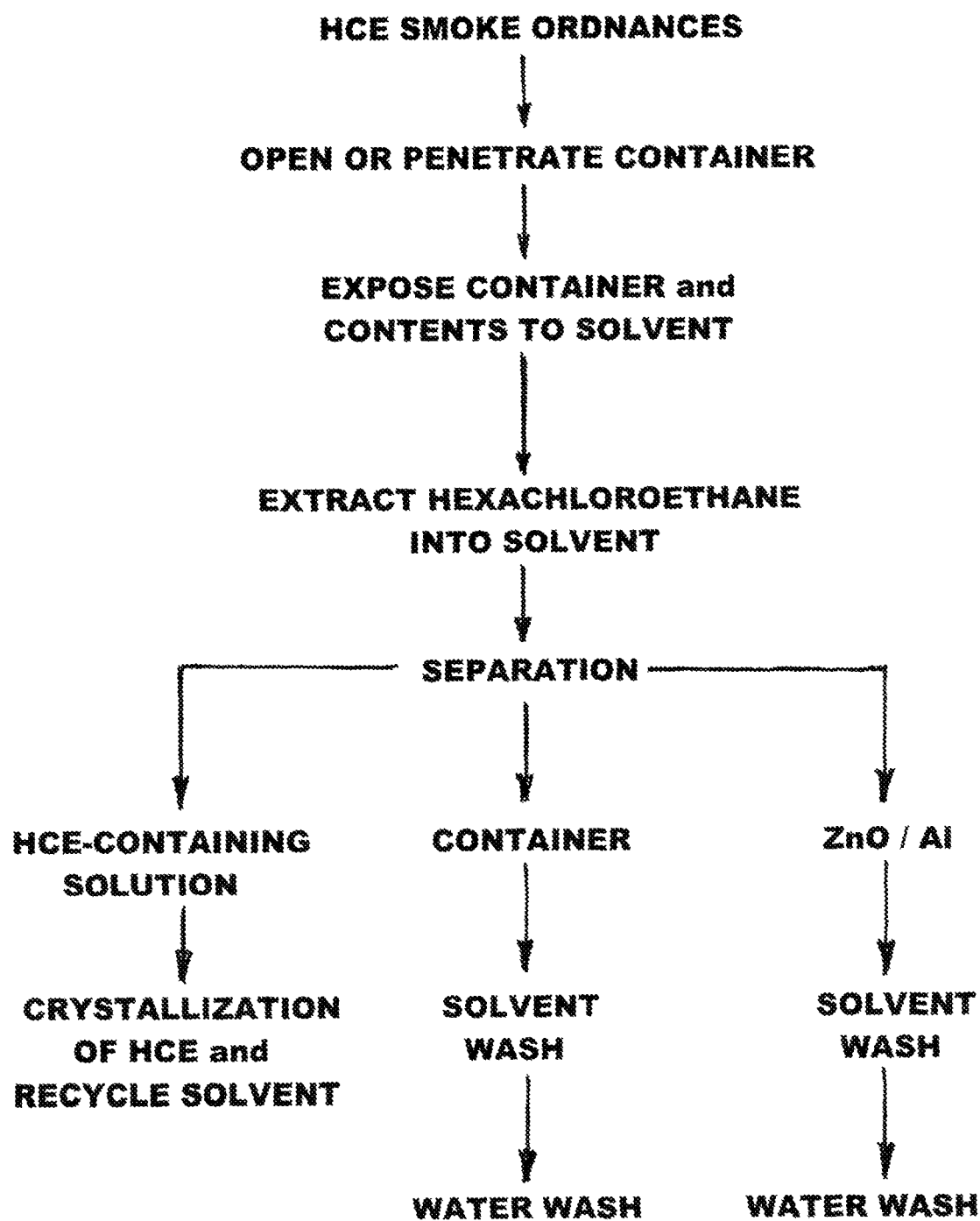
FIG. 2 is a schematic drawing of the invented method showing additional process steps.

However, much more desirably the contents of the ordnance can be recycled and reused as shown in FIG. 2. There is a market for the hexachloroethane, for example as an intermediate for the manufacture of foundry fluxes. There are also markets for zinc, and the grained or granular aluminum, after separation, is reusable as is. The steel containers are also salvageable as steel scrap. Grenade bodies are generally iron, which is salvageable, and artillery projectiles (shells) are steel or other alloy, which again is salvageable as scrap metal. The only non-recyclable materials are the fuse and igniter, which make up much less than 1% of the ordnance. There are many markets for zinc products, provided their purity does not violate environmental requirements.

It is highly preferable to separate and remove the HCE from the mix first, as it is usually the substance with the most hazardous properties: (1) it has the most limited PEL (permissable exposure limit) in air; (2) if heated to 300 C (572 F), it decomposes into very noxious vapors which include suspected human carcinogens, and air toxics such as phosgene; and (3) when it is removed, the remaining substances are easily separable.

Steps of the invented method for the demilitarization of the HC smoke ordnances, and recycle of the constituents are:

1. Open or penetrate the steel containers, exposing the container and its contents to a solvent, preferably by immersion in the solvent, and dissolving the Hexachloroethane (HCE). With the opened container solvent wetted, and the HCE dissolved, the HC smoke ordnance cannot operate, promoting a much safer material for process continuance. A suitable solvent is that which solubilizes and extracts the HCE from the remaining zinc oxide and aluminum, such as chloroform. This step alone achieves demilitarization of the HC smoke ordnance.

2. Remove the solvent/HCE solution from the remainder of the mix and the opened containers. Filter out the ZnO and Al from the solvent/HCE solution. Heat the solvent to its boiling point and vaporize the solvent, leaving high purity HCE in solid form. Cool and recycle the solvent.

3. Parts of the igniters are water soluble, and soaking the igniters in solvent then in water further prevents their accidental activation.

4. Solvent wash, then water wash the container scrap and the zinc oxide/aluminum to remove the wetting solvent/HCE solution. Reuse the wash solvent internally and filter the wash water through activated carbon to remove traces of HCE. Regenerate and reactivate the carbon.

5. In a quality assurance step, the scrap metal and the residue of the igniters are warmed to an acceptable temperature to verify that the designated material is safe to be recycled as scrap. At this point the HC smoke pot has been demilitarized and the remainder can be landfilled.

6. Physically separate the aluminum from the zinc oxide, the latter of which may need to be put in slurry form first, water wash the granular aluminum and market the aluminum. Internally reuse the wash water.

7. Further refine the water-wet zinc oxide. At this point, more than 99% of the HC smoke ordnance has been recycled.

The aforesaid 7 steps achieve the results of:

1. Demilitarizing and deactivating HC ordnances sufficiently for disposal into a landfill: and 2. Allowing recycling of demilitarized materials and reagents used in the process.

The solvent is selected from the group consisting of: chlorinated hydrocarbons, alcohols, and other organic solvents having the ability to dissolve hexachloroethane (HCE). Suitable solvents include, but are not necessarily limited to: chloroform, 1-octanol, 1,2-dibromoethane, 1,2-dichloroethane, 2-methylpentane, 2,2-dimethylbutane, 2,3-dimethylbutane, 3,methylpentane, benzene, carbon disulfide, carbon tetrachloride, chlorobenzene, cis-1,2-dimethylcyclohexane, cis-1,3-dimethylcyclohexane, cis-1,4-dimethylcyclohexane, cyclohexane, dichloroethane, dichloromethane, ethylbenzene, heptane, hexane, methylcyclohexane, octane, toluene, trans-1,2-dimethylcyclohexane, perchloroethylene, and trans-1,4-dimethylcyclohexane.

SUMMARY OF THE ACHIEVEMENT OF THE OBJECTS OF THE INVENTION

From the foregoing, it is readily apparent that I have invented an improved method for deactivating HC smoke ordnances, as well as a method for recovery of zinc values and aluminum metal from HC smoke ordnance.

It is to be understood that the foregoing description and specific embodiments are merely illustrative of the best mode of the invention and the principles thereof, and that various modifications and additions may be made to the process and apparatus by those skilled in the art, without departing from the spirit and scope of this invention.

What is claimed is:

1. A method for demilitarization of HC smoke ordnance comprising hexachloroethane (HCE), zinc oxide, and granular aluminum in a metal container, said method comprising:
    open or penetrate the container and extract the HCE by contact with a solvent which solubilizes and extracts the HCE from the zinc oxide and aluminum; and
    wherein the solvent is selected from the group consisting of: chloroform, benzene, carbon disulfide, carbon tetrachloride, and perchloroethylene.

2. A method according to claim 1, wherein the solvent has a boiling point significantly below that required to ignite HC smoke mix.

3. A method according to claim 2, wherein the solvent has a boiling point at least 30° C. less than the temperature below that required to ignite HC smoke mix.

4. A method according to claim 1, wherein said HCE smoke ordnance contains an igniter, said method further comprising after extraction of HCE, the step of heating the metal container and the igniter to a temperature of at least 300 C to verify that they are safe material for recycling.

5. A method according to claim 1, wherein the container is principally iron or steel.

6. A method for demilitarization of HC smoke ordnance comprising hexachloroethane (HCE), zinc oxide, and granular aluminum in a metal container, said method comprising the steps of:
    a) open or penetrate the container to expose its contents; and
    b) contact the container and its exposed contents with a solvent and dissolve the hexachloroethane, and form a hexachloroethane solution, thereby demilitarizing said ordnance;
    wherein the solvent is selected from the group consisting of: chloroform, benzene, carbon disulfide, carbon tetrachloride, and perchloroethylene.

7. A method according to claim 6, further comprising:
    filtering the HCE solution from the ZnO and Al leaving ZnO/Al solids;
    heating the solvent to its boiling point and vaporizing the solvent leaving high purity HCE in solid form.

8. A method according to claim 7, further comprising recovering and recycling the solvent.

9. A method according to claim 6, further comprising:
    washing the container and the ZnO/Al with solvent, followed by washing the container and the ZnO/Al with water to remove the solvent/HCE solution, resulting in deactivation of the HCE smoke ordnance.

10. A method according to claim 6, wherein said HCE smoke ordnance contains an igniter, said method further comprising exposing the chemical components of the igniter, then soaking the chemical components of the igniter in solvent, then in water to prevent accidental activation.

11. A method according to claim 6, further comprising:
    separating the aluminum from the zinc oxide leaving an impure zinc oxide sludge, and recovering the aluminum as metal.

12. A method according to claim 6, wherein the container is principally iron or steel.

13. A method according to claim 6, wherein the solvent has a boiling point significantly below that required to ignite HC smoke mix.

14. A method according to claim 13, wherein the solvent has a boiling point at least 30° C. less than the temperature below that required to ignite HC smoke mix.

15. A method according to claim 13, wherein the solvent has a boiling point at least 60° C. less than the temperature below that required to ignite HC smoke mix.

* * * * *